United States Patent [19]

Brownlee

[11] Patent Number: 5,127,403
[45] Date of Patent: Jul. 7, 1992

[54] PACEMAKER CATHETER UTILIZING BIPOLAR ELECTRODES SPACED IN ACCORDANCE TO THE LENGTH OF A HEART DEPOLARIZATION SIGNAL

[75] Inventor: Robert R. Brownlee, Ormond Beach, Fla.

[73] Assignee: Cardiac Control Systems, Inc., Palm Coast, Fla.

[21] Appl. No.: 570,540

[22] Filed: Aug. 21, 1990

Related U.S. Application Data

[63] Continuation-in-part of Ser. No. 333,085, Apr. 4, 1989, Pat. No. 4,962,767, which is a continuation-in-part of Ser. No. 215,258, Jul. 5, 1988, abandoned.

[51] Int. Cl.⁵ .............................................. A61N 1/05
[52] U.S. Cl. ................................. 128/419 P; 128/696; 128/642
[58] Field of Search ............... 128/783, 784, 786, 639, 128/642, 419 P, 419 PG, 696

[56] References Cited

U.S. PATENT DOCUMENTS

| | | | |
|---|---|---|---|
| 3,825,015 | 7/1974 | Berkovits | 128/404 |
| 3,903,897 | 9/1975 | Woollons et al. | 128/419 |
| 3,911,928 | 10/1975 | Lagergren | 128/418 |
| 3,915,174 | 10/1975 | Preston | 128/419 |
| 3,942,536 | 3/1976 | Mirowski et al. | 128/419 |
| 3,995,623 | 12/1976 | Blake et al. | 128/216 |
| 4,010,755 | 3/1977 | Preston | 128/404 |
| 4,091,817 | 5/1978 | Thaler | 128/419 |
| 4,355,646 | 10/1982 | Kallok et al. | 128/786 |
| 4,365,639 | 12/1982 | Goldreyer | 128/786 |
| 4,394,866 | 7/1983 | Hughes | 128/785 |
| 4,444,195 | 4/1984 | Gold | 128/642 |
| 4,499,907 | 2/1985 | Kallok et al. | 128/786 |
| 4,585,004 | 4/1986 | Brownlee | 128/419 |
| 4,595,012 | 6/1985 | Webler et al. | 128/642 |
| 4,608,986 | 9/1986 | Beranek et al. | 128/786 |
| 4,630,611 | 12/1986 | King | 128/642 |
| 4,686,987 | 7/1987 | Salo et al. | 128/419 |
| 4,754,753 | 7/1988 | King | 128/699 |
| 4,759,367 | 7/1988 | Callaghan | 128/419 |

OTHER PUBLICATIONS

A New Orthogonal Lead for P Synchronous Pacing, Bruce N. Goldreyer, et al. PACE vol. 4, Nov.-Dec. 1981.

Primary Examiner—William E. Kamm
Assistant Examiner—Kennedy J. Schaetzle
Attorney, Agent, or Firm—Kerkam, Stowell, Kondracki & Clarke

[57] ABSTRACT

A catheter lead for a cardiac pacemaker in which stimulating pulses are generated for delivery to the heart according to physiological need of the patient determined by signals obtained solely from the detection of naturally occurring P-waves propagating through the atrial myocardial tissue.

4 Claims, 5 Drawing Sheets

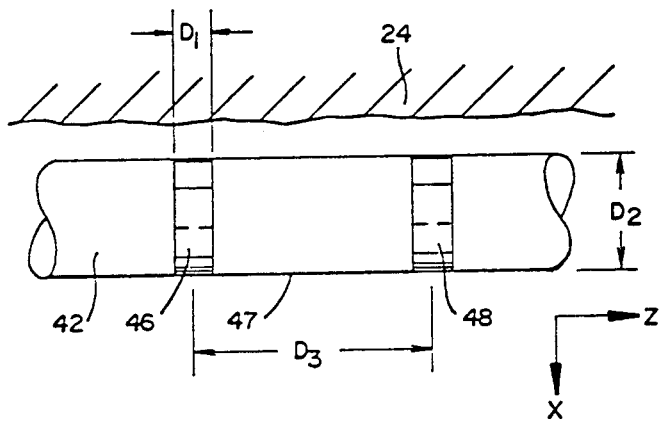
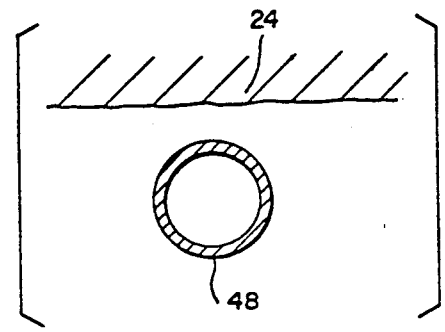
FIG 3A
FIG 3B
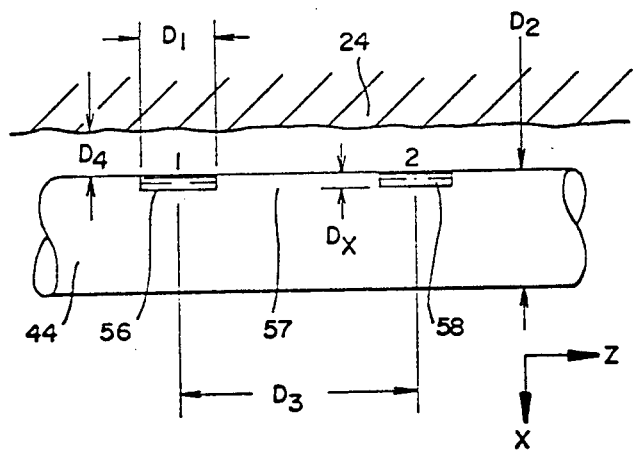
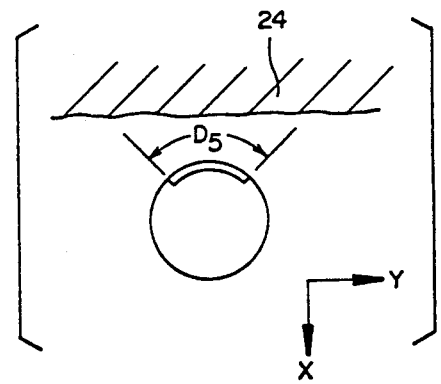
FIG 5A
FIG 5B

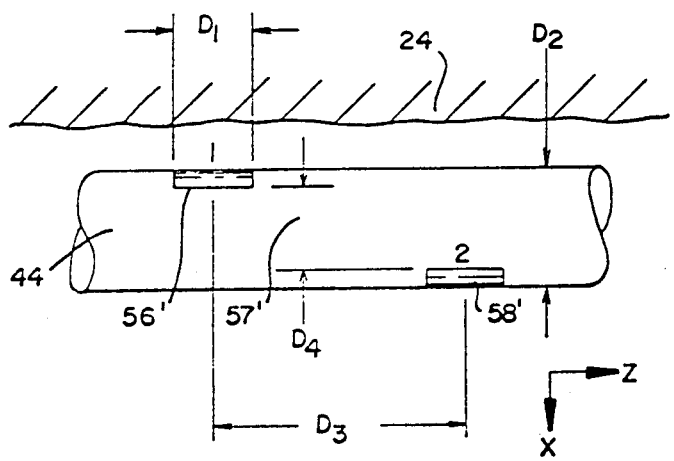
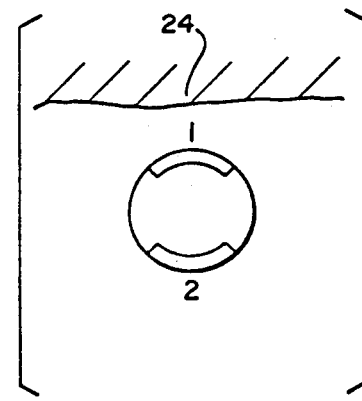
FIG 6A  FIG 6B
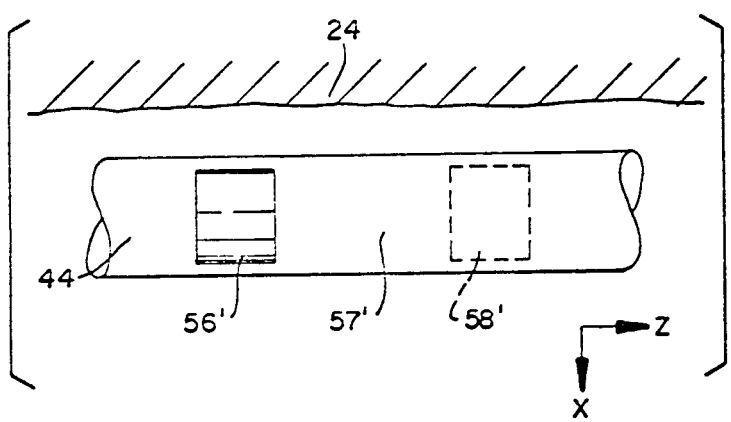
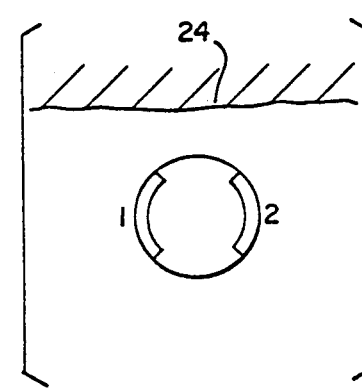
FIG 6C  FIG 6D
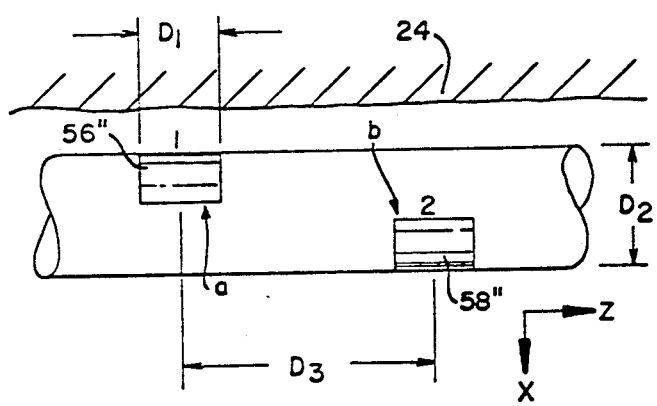
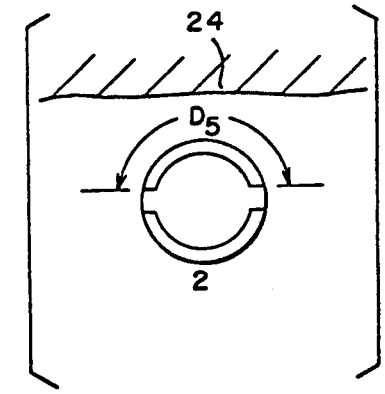
FIG 7A  FIG 7B

PACEMAKER CATHETER UTILIZING BIPOLAR ELECTRODES SPACED IN ACCORDANCE TO THE LENGTH OF A HEART DEPOLARIZATION SIGNAL

CROSS-REFERENCES TO RELATED APPLICATIONS

This application is a continuation-in-part of my application Ser. No. 333,085, filed Apr. 4, 1989, now U.S. Pat. No. 4,962,767 which is a continuation-in-part of application Ser. No. 215,258, filed Jul. 5, 1988, (now abandoned), and related subject matter is claimed in co-pending application Ser. No. 557,792, filed Jul. 29, 1990.

BACKGROUND OF THE INVENTION

This invention relates to cardiac pacemakers and, more particularly, to the orientation and shape of the electrodes of a pacemaker catheter.

Cardiac pacemakers have been extensively used in patients with poorly functioning heart pacing mechanisms due to breakdown in the cardiac electrophysiological system. The pacemakers rectify malfunctioning systems by stimulating the heart with electrical impulses and thus controlling the heart beat rate.

In normal functioning cardiovascular systems, electrical signals are produced by the sino-atrial (S-A) node. The S-A node controls the heart beat by stimulating the heart muscles through electrical signals of sufficient magnitude and accurate sequential timing. The electrical signals are conducted from the S-A node to the right and left atria, and are also transmitted from the atria through the AV node to the right and left ventricles, which respond to the depolarizing wave and produce contraction of the heart muscle. Malfunction in the AV node conduction system between atrium and ventricle sometimes results in failure or block of the transmitted signal. Simple cardiac pacemakers supply a stimulus signal to the ventricle and thus cause the heart to beat at a fixed rate.

Various other cardiac pacemaker system types have been used in the past, and the most widely used of these are discussed in U.S. Pat. No. 4,365,639 to Goldreyer. One such system uses two catheters, one positioned in the ventricle and the other within the atrium, respectively. The stimulating electrodes disposed on each of the catheters were operated at a set rate, and with a time lag between the stimulating pulses. Several drawbacks to such a sequential pacing system were discovered, among them that two catheters were necessary for implantation in the heart and that cardiac output was only augmented by about 5 to 15% with fixed rate pacing. Also, two catheters were found to be overly bulky and, furthermore, because the system only operated at a rate fixed by the pacemaker, the heart could not compensate by increasing the heart beat rate if the patient experienced increased activity.

Other systems relied on a sensing mechanism where the cardiac pacemaker had both stimulating and sensing electrodes, or alternatively, one of the electrodes could act both as a sensor and as a stimulator. For these types of systems, the sensor would be set to sense a certain type of distinctive electrical wave pattern, known as a P-wave associated with atrial depolarization, which is the signal sent to the heart muscle in the ventricle via the AV node which causes the ventricle to contract. If a distinctive P-wave is sensed after a predetermined time interval from the last P-wave, the stimulating electrodes would then supply a pulse of energy of sufficient magnitude to stimulate the heart muscle into contraction at the proper time in the heart beat cycle.

With these types of systems, however, it becomes increasingly important that the electrical signal be detected accurately and consistently. Several of the aforementioned systems, as well as others, have emphasized the basic subject of endocavitary detection of cardiac signatures of the electrical signals associated with cardiac depolarization. Optimization of detection of signals in the atrial chamber of the heart is of particular importance because of the weak signals obtainable from the traveling wave front along the atrial myocardial wall during atrial depolarization.

Aforementioned U.S. Pat. No. 4,365,639 discloses a method to detect signals in the heart by the use of electrodes normal (orthogonal) to the plane of the depolarizing wave in the atrial cardiac tissue. However, the configuration of the electrodes on the catheter, and especially their shape and orientation in relation to each other, failed to take advantage of characteristics peculiar to the electrical signatures of cardiac waves in order to more accurately and consistently detect the signals indicative of a traveling wave front, such as a P-wave. Accordingly, it is an object of the present invention to improve the detection of physiologic electrical signals by optimizing the electrode configuration over that known to the prior art.

It is another object of the present invention to increase the sensitivity of a P-wave detection mechanism for providing a signal indicative of the passing of a P-wave to a cardiac pacer.

It is yet another object of the present invention to provide a catheter for a cardiac pacemaker system which takes into account various factors such as the extracellular potential field dimensions, the propagation direction of the field, anomalies in the conducting muscle fiber associated with age, and the practical impedance level of the electrodes as it relates to the electrode surface area, as well as to other factors.

It is still another object of the present invention to provide a new and improved electrode system which will provide for varying the heart rate in response to the body demand while at the same time utilizing only a single catheter inserted through a vein, without necessitating open heart surgery. A particular object of the invention is to provide an improved sensing electrode arrangement for detection of P-wave signals for controlling the timing of ventricular stimulation.

It is also an object of the present invention to provide a catheter for sensing and for stimulation in the form of a single non-diverging filament having two sensing electrodes mounted on the catheter with optimal placement, shape, size and orientation of the catheter electrodes.

It is a further object of this invention to provide for electrode sizes that are small as practical relative to the dimensions of the width of the traveling wave front and small relative to the dimensions of the field gradient normal to the wall of depolarizing muscle.

It is yet another object and a significant advantage of the present invention to optimize the parameters of the catheter electrodes in a pacemaker system so as to increase the effectiveness of the cardiac pacemaker system.

It is also an advantage of the present invention to adjust the placement, shape and orientation of the electrodes on a catheter of a cardiac pacemaker system so as to tune the electrode parameters to the peak negative to peak positive distance in the sensed traveling wave front of the depolarizing wave indicative of the physiologic signals creating a heart beat.

It is a further advantage and a unique feature of the present invention to allow the adjustment of the catheter electrode parameters so as to be suitable for the individuals having a variety of ages, heart sizes and heart conditions.

It is another feature of the present invention to provide optimal size, placement and orientation of the atrial electrode array so as to fully take advantage of the characteristics of the P-wave to improve sensing effectiveness.

In accordance with these and other objects, features and advantages of the present invention, there is provided a catheter for use in a cardiac pacemaker system with electrode pair arrangements limited to two electrodes operating together in a direct or differential bipolar configuration for sensing cardiac depolarization in the blood pool and not requiring contact with cardiac tissue.

The electrodes are so configured on the catheter relative to the cardiac depolarization wavefront direction to prevent signal cancellation or excess signal mitigation when the signals sensed from each electrode of the pair are electronically subtracted.

The electrode pair is configured so that the electrodes are placed on opposite sides of the catheter body but displaced longitudinally equal to or greater than the length of the depolarization signal along the axis of the catheter and more or less parallel to the axis of depolarization to allow the combinational features of controlling the electrode dimensions in all three planes to minimize field averaging in all planes and to prevent signal cancellation as the depolarization wave passes each electrode.

The invention will be better understood and additional objects, features and advantages will become apparent from the following description of the preferred embodiments with particular reference to the drawing figures, wherein like referenced numerals indicate like elements.

BRIEF DESCRIPTION OF THE DRAWINGS

FIGS. 3A and 3B show detailed side and end views, respectively, of the embodiment shown in FIG. 2.

FIGS. 5A and 5B illustrate detailed side and end views, respectively, of another embodiment of the catheter electrodes according to the invention.

FIGS. 6A and 6B illustrate detailed side and end views, respectively, of another embodiment of the catheter having the electrodes disposed on opposite sides of the filament.

FIGS. 6C and 6D show the catheter oriented in a 90° rotation from FIGS. 6A and 6B, respectively, in relation to the atrial wall.

FIGS. 7A and 7B illustrate detailed side and end views, respectively, of an embodiment similar to that of FIGS. 6A through 6D and having electrodes disposed as hemicyclical extensions substantially around one half of the circumference of the catheter.

DETAILED DESCRIPTION OF THE INVENTION

Theoretical electrical field theory regarding the signatures of the bioelectric phenomena associated with muscle or nerve depolarization has been studied to better understand the propagation of electrical signals through tissue membranes. Studies have shown that the electrode-sensed surface potential along the axis of a depolarizing wave can be diphasic or triphasic, depending on the rate of change of rise and decay of the depolarizing field. The decay rate, or repolarization of cardiac muscle tissue, has been found to be slow so that electrode-sensed extracellular intrinsic deflections are normally diphasic. This diphasic nature of the normal intrinsic signature can be advantageously employed in bipolar systems to detect atrial depolarization by spacing, or tuning, the electrode separation equal to the peak-negative-to-peak-positive dimension of the extracellular wave form.

Figure 1A:
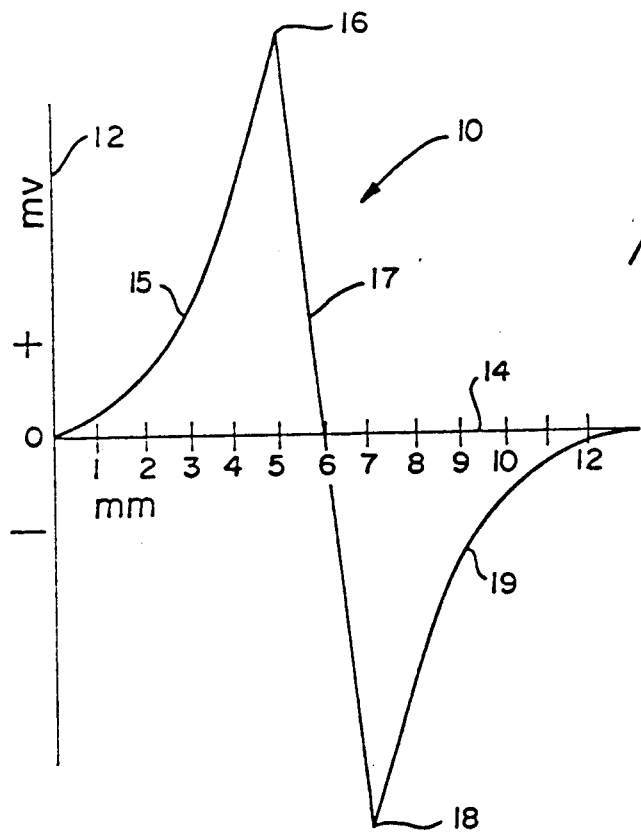
FIG. 1A illustrates a graph of an idealized extracellular wave form generated by the action potential as it propagates in the heart.

FIG. 1A illustrates an idealized extracellular waveform generated adjacent to heart muscle tissue by the action potential, using approximate dimensions. FIG. 1A is a graph of the extracellular potential, measured in millivolts along the Y-axis 12, as a function of the longitudinal distance in the medium in which the wave form is traveling, as measured in millimeters (mm) along the X-axis 14. For optimum P-wave sensing, the cardiac pacemaker system includes circuitry for the differential processing of the sensed signal. As the diphasic wave front passes a catheter electrode pair according to the present invention, the opposite peak polarities are added when the signal is differentially processed, thus providing a more accurate and effective sensor of the passing extracellular potential waveform.

The present invention includes characteristics and elements tending to take advantage of the summation effect between the peak-positive 16 and peak-negative 18 potentials so as to more accurately sense the depolarization wave even when it is weak in relation to a normal depolarization wave.

As shown in FIG. 1A, one peak maximum positive 16 and one peak maximum negative 18 field signals occur in time if an electrode is placed in the wave front of the moving depolarizing wave, shown generally by reference numeral 10. For purposes of this invention, the distance between maximums peaks 16, 18 is defined as the one-half wave length of the sensed total depolarization wave, or the 2 mm distance traversed by the wave form, as shown by line 17 in FIG. 1A. This definition is useful since the wave form is not sinusoidal and not continuous periodic, as is the usual case for transmission of radio-frequency energy through space. For instance, the upward slope 15 or 19 of the measured potential across the electrode is less steep than that of the intrinsic deflection line 17.

Figure 1B:
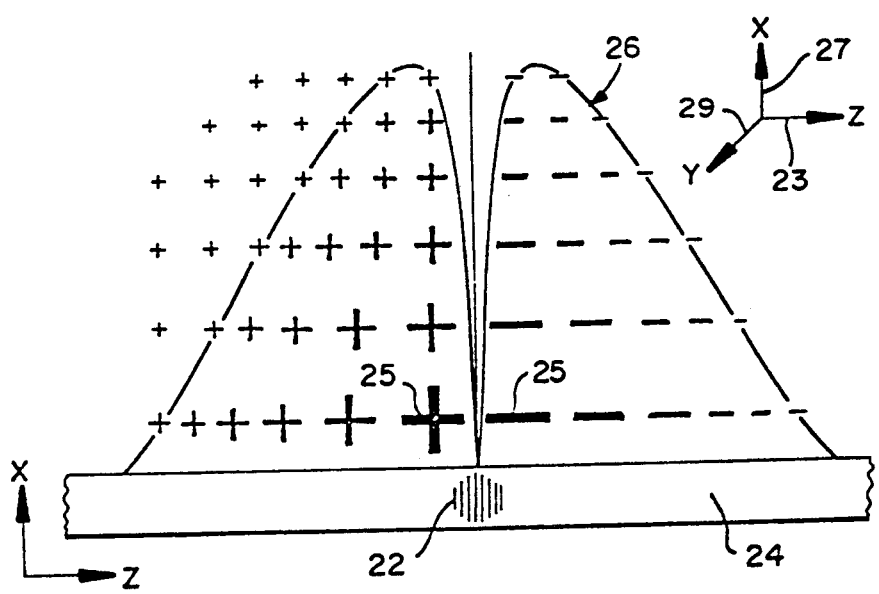
FIG. 1B illustrates a simplified model of a propagating extracellular potential along the atrial wall.

Referring now to FIG. 1B, the traveling wave front is represented by cross-hatching 22 traveling in the atrial wall 24 in the direction of the arrow Z. The wave front 22 creates an electric field in the space adjoining the atrial wall. This electric field is strongest close to the atrial wall 24, as is represented by the plus and minus signs marked in bold 25 and decreases with the distance from the point in the atrial wall where the depolarization is instantaneously occurring. The electric field is attenuated by the medium in which it is shown, in this case, the blood contained within the atrium, and is represented as completely essentially dissipating around a loosely defined boundary represented by dashed line 26. Definition of the various spatial directions may be understood from the representation of the X-direction 27 and Z-direction 23. The wave front 22 travels in the Z-direction 23 and the field is manifested in the X-direction 27 and Y-direction 29 (out of the plane of the paper).

It is also necessary to take into account that the traveling electric wave in a biologic system is to be sensed with highly conductive metal electrodes placed within a volume conductor medium (i.e., blood or body tissue) in which the field potentials are developed. The interface between electrode and medium interface is quite complex and principally capacitive in impedance but it is hypothesized that electrodes of dimension that exceed the wave front dimension in the X and Z planes of the wave front distort the wave front potentials and averaging of the gradient along the axis and perpendicular to the axis of the wave front occurs, creating signal attenuation compared with a result that would be achieved with point source electrodes.

Figure 2:
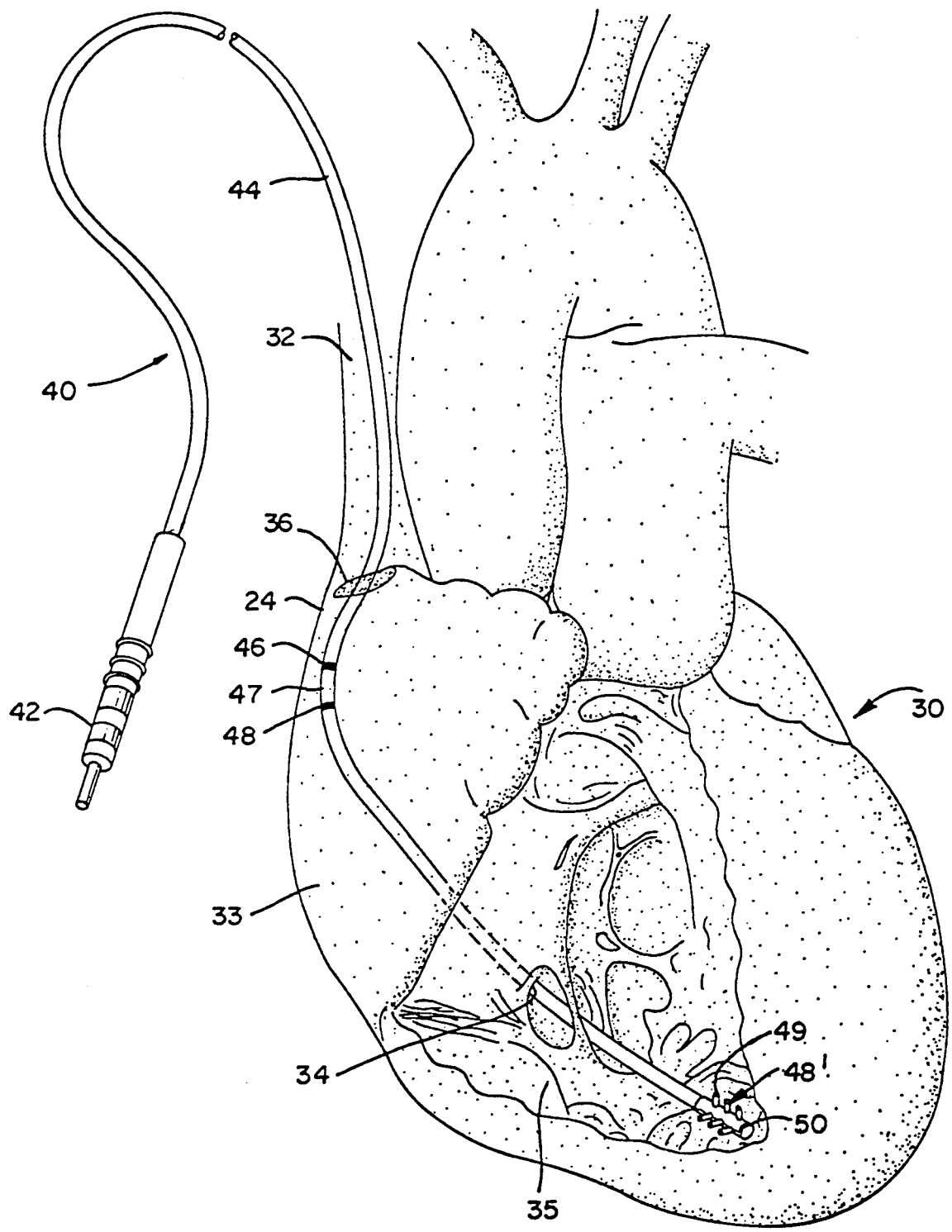
FIG. 2 illustrates an embodiment of the device according to the present invention inserted into a patient's heart which is shown in a partial cut-away view.

FIG. 2 illustrates the heart of a patient, generally indicated at 30, having a number of chambers, but principally the right atrium 33 and the right ventricle 35, shown in partial cut-away views, and the superior vena cava 32, a major vein, connected to right atrium 33. The heart 30 has a catheter 40 implanted through the superior vena cava 32. The sino-atrial (S-A) node 36, at the blood fluid entrance to the atrium 33, depolarizes and initiates a depolarization wave front along the atrial wall 24, substantially as shown in the idealized model of FIG. 1B.

The catheter 40 comprises an in-line tri-axial connector 42, a single, flexible, non-diverging, coaxial insulated conductor 44 having two sensing electrodes 46, 48, a coaxial insulated conductor portion 47 between electrodes 46, 48, and a distal electrode 50 at the tip of a single insulated conductor 44. Detachment member 48', made of a flexible material having flexible projections 49 projecting normal to and disposed around filament 44 adjacent distal electrode 50, is provided to maintain a stable position in the ventricle.

The catheter 40 is surgically inserted into the patient's heart 30 through the superior vena cava 32, past the S-A node 36, and into the right atrium 33. The distal end, with electrode 50, is further inserted into the right ventricle 35 through the tricuspid valve annulus 34. In the embodiment illustrated in FIG. 2, both sensing electrodes 46, 48 are disposed completely within the right atrium 33, and the axis of the catheter electrode pair 46, 48 is parallel to the direction of the propagating action potential (Z-direction) in the region of the electrodes.

Even when the electrodes are spaced along the axis of the lead, i.e., essentially parallel to the general axis of depolarization along the Z-direction, another concern is the uncertainty of the conduction direction and of the sensed signal morphologies in the region of the electrodes, as the heart tissue is a non-isotropic medium. These uncertainties become more prevalent in the aging heart. The conduction velocity of cardiac depolarization is known to be much higher in the direction of the axis of muscle fiber compared to across the muscle fibers. When this property is coupled with increased discontinuities in the muscle associated with aging, the uncertainty of the direction of propagation in the region of an arbitrary electrode pair site increases. The signal morphology (i.e., shape and polarity of each signal) as sensed on each electrode can also become complex in an anisotropic medium, and additive signatures cannot be guaranteed.

For optimum detection of signals from healthy atrial myocardium, it is preferable to space bipolar electrodes, such as 46, 48 closely together, i.e., tuned to the peak-negative-to-peak-positive dimensions of the extracellular wave form shown in FIG. 1A. For the aging heart, the uncertainties of propagation direction and signal morphology point toward an electrode spacing that exceeds the normal wave front dimensions. The probability of achieving instantaneous additive signals on an electrode pair would diminish as the dimensions between electrodes increase, but the probability of encountering subtractive signals would also diminish. Thus the increased spacing of the electrodes in an aging heart is a worthy trade-off in a system where it is desirable to detect every atrial depolarization cycle to maintain one-to-one atrial synchronized ventricular pacing.

The subject of electrode size and shape for optimizing detection of extracellular potentials is complicated by the practical reality of having to connect the electrodes 46, 48, 50 through the triaxial connector 42, and triaxial catheter 44 to a system in which the system impedance level cannot be guaranteed to remain high. Chronically implanted pacemaker systems are subject to fluid entry into the non-hermetic elements of the system. The connector header assembly and the lead system used to connect the electrodes to the processing electronics are both subject to the body fluid environments. The materials comprising the leads and connector header assembly elements are permeable to fluid entry over longer periods of time, leading to potential fluid bridging across the various electrical interconnecting points.

Ideally, electrodes should be very small relative to the dimensions between the peaks of the extracellular action potential because large electrodes average unequal isopotential lines over a large area. It is hypothesized that if electrodes instantaneously project through isopotential lines of different amplitudes, the maximum amplitude available from the detected extracellular signal would be reduced due to averaging of the peak isopotential line with lines of lower amplitude. Furthermore, the frequency content of the signal generated on an electrode as an extracellular wave form passes is related to both the length of the electrode in the direction of propagation and the conduction velocity of the wave form. Stated another way, the action potential signal duration is artificially extended by the transit time of the propagating wave over the length of the electrode.

The theoretically perfect bipolar electrode pair for sensing atrial signals would be infinitely small individual electrodes with an axis between the pair oriented parallel to the axis of depolarization, and the distance between these electrodes should be set to equal the peak-negative-to-peak-positive dimension of the extracellular wave form. Further, each sensing electrode should be set directly on the atrial wall.

Unfortunately, this perfect configuration is not practical for placement on a pacing catheter and for dealing with the necessity of providing a reasonably low impedance level needed for implantable pacemaker applications. For such applications, electrode surface areas smaller than about 4 mm² are impractical. Differential processing is particularly sensitive to phase imbalances if chronic fluid bridging of the implanted system were to result in unbalanced loading of the electrode pair. Also, because the electrodes are to be placed on the circumference of a pacing catheter in which the angular orientation cannot be assured, the configuration choices to approach the ideal become practically limited to ring electrodes or electrodes opposed and longitudinally spaced apart on the catheter.

The embodiment shown in FIGS. 3A and 3B are two circumferential ring electrodes which are shown in greater detail than in FIG. 2, and more distinctly point out inventive aspects of the invention. The unique features of this ring configuration of electrodes include the dimensions of and the spacing between the ring electrodes 46, 48. To optimize signal detection, the ring electrode widths ($D_1$) should be as small as possible consistent with a desire to maintain an electrode surface area of 4 to 6 mm². It would, if possible, also be desirable to limit the ring electrode diameter ($D_2$) to prevent averaging of the extracellular field potential normal to the atrial wall 24 (X-direction). However, triaxial pacing catheters have practical limits of about 2 mm diameter. With a ring electrode diameter of 2 mm, the ring width has to be on the order of 1 mm to provide an overall surface area in the 6 mm² range, the desired surface area to maintain an adequately low source impedance level for use in the chronic implant environment.

The insulated filament portion 47 and spacing between the ring electrodes ($D_3$) provide the benefit of tuning to the peak-negative-to-peak-positive dimensions of the extracellular wave form which is optimally on the order of 2 to 3 mm. If intramyocardial conduction disturbances are suspected related to those encountered in aging cardiac muscle, the spacing between rings should be increased to 4 to 5 mm to mitigate the potential of signal subtraction caused by a circuitous conduction path between electrodes and/or by abnormal signal morphologies detected on each electrode related to propagation in an anisotropic medium.

Another inventive feature of the device as herein disclosed is tuning the electrode spacing in the Z-plane, i.e., in the direction parallel to the wave front, in order to match the peak-negative to peak-positive fields of the traveling wave front. The method of orthogonal detection in contrast can only be optimized by spacing the electrodes at the largest practical dimension across the lead body of the catheter. Orthogonal detection with bipolar electrodes measures the differential gradient potential of the traveling wave front in a plane normal to the wave front. An orthogonal electrode pair can also be signal subtractive when processed differentially depending on the angular orientation of the catheter.

Figure 4:
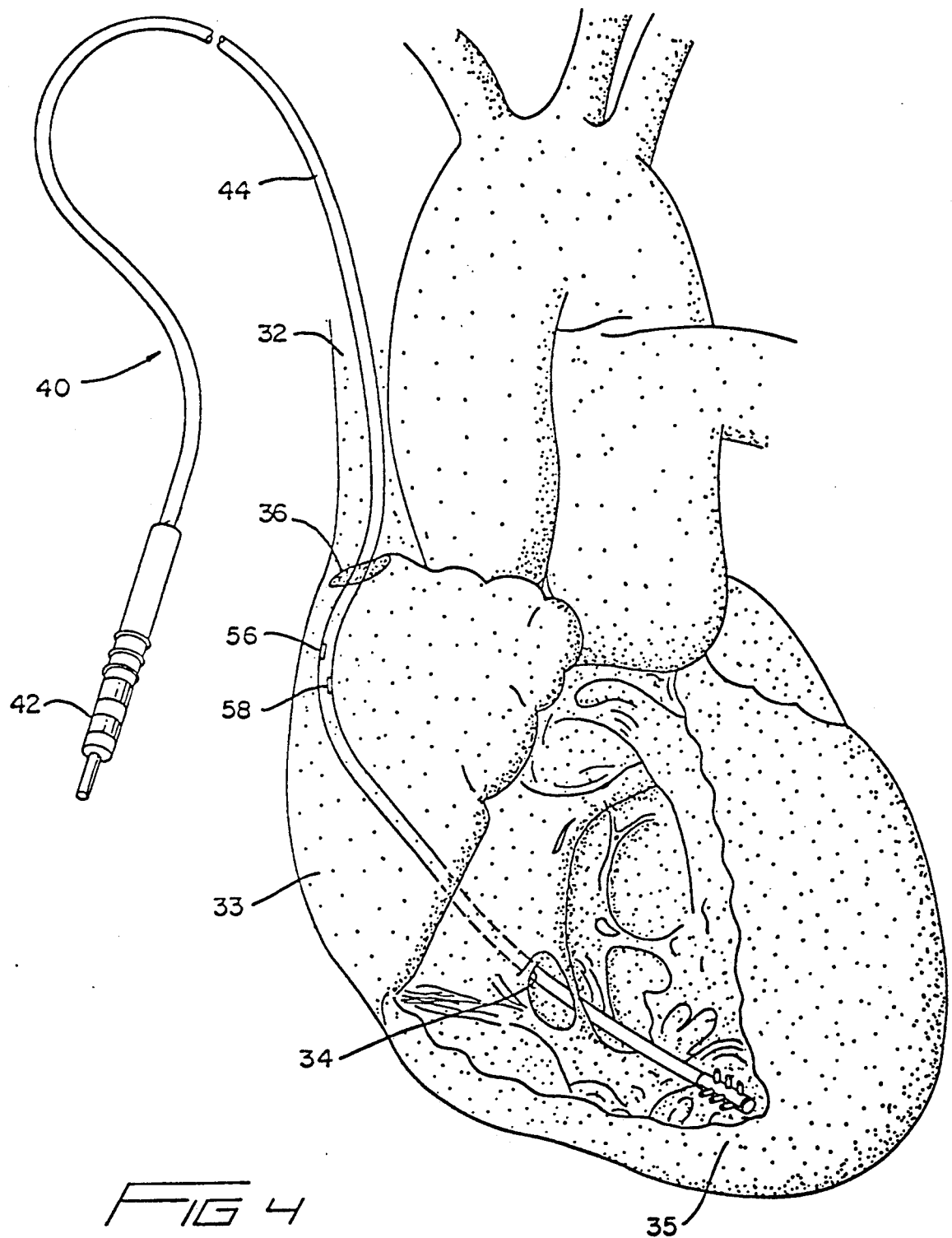
FIG. 4 illustrates another embodiment of the device according to the present invention inserted into a patient's heart.

Referring now to FIG. 4, the general direction of normal antegrade conduction in the atrium 33 is from the S-A node 36 toward the right ventricle 35. Thus, it is inherently better to space electrodes 56, 58 along the axis of filament 44, that is, parallel to this normal propagation direction, rather than circumferentially around the filament. The longitudinal orientation also allows greater freedom in choosing an optimum spacing between electrodes 56, 58 because the choice is not restricted to the filament diameter. In the circumferential (i.e., orthogonal) configuration, it is likely that signal substraction can occur at least intermittently, since nearly identical extracellular waveforms can pass the electrodes at the same instant in time, if both electrodes are equidistant from the atrial wall.

One embodiment of the invention using non-circumferential electrodes is shown in FIGS. 5A and 5B. This embodiment would be preferable to ring electrodes if the angular orientation of the catheter filament 44 in relation to atrial wall 24 could be maintained so that electrodes 56, 58 remain adjacent the atrial wall 24, as shown. The smaller electrode dimension in the X direction (DX) minimizes averaging of unequal isopotential lines of the extracellular wave form normal to the atrial wall 24. The dimensions $D_1$, or length of electrodes 56, 58, should be minimized to prevent averaging of unequal isopotential lines in the Z plane. To maintain equivalency in surface area with the embodiment shown in FIGS. 3A and 3B, the dimensions $D_5$ and $D_1$ have to multiply to 6 mm².

The absolute optimum shape factor relies on a greater understanding of the electric field equations that define both the X and Z variables of the extracellular field shape. Of perhaps greater technical concern is the effect the electrodes 56, 58 and the insulated filament 57 have on the field shape. Like so many measurement situations encountered in science, the measurement apparatus becomes a part of the problem to be solved. However, since the angle between the axis of the electrodes and the direction of propagation cannot be known for certain, equal linear dimensions for $D_5$ and $D_1$ to achieve 6 mm² are most probably appropriate. The design to achieve a 6 mm² surface area requires about a 2.5 mm by 2.5 mm linear dimension for $D_1$ and $D_5$. The choice for the dimensions between electrodes 56, 58, i.e., ($D_3$), depends on the same arguments used for the ring electrodes 46, 48 of FIG. 3B. That is, $D_3$ should be either tuned to the action potential dimensions of 2 to 3 mm, or set apart greater than 3 mm to prevent signal cancellation. The difficulty in the embodiment shown in FIGS. 5A and 5B arises in maintaining the electrodes 56, 58 next to the atrial wall 24.

FIGS. 6A and 6B show another embodiment being an optimal compromise of the embodiments shown in FIGS. 3A, 3B and FIGS. 5A and 5B. This embodiment takes into account the possibility of rotation of filament 44 with respect to the atrial wall 24, and disposes hemicyclical electrodes 56', 58' on opposite sides of filament 44. Like that of the ring electrodes 46, 48, shown in FIGS. 3A and 3B, this configuration is relatively forgiving of angular rotation of the catheter filament 44, since either one or both electrodes can be apposed to the atrial wall 24. For example, if only one electrode is apposed to the wall, significant signal addition is unlikely because the second electrode is separated from the wall 24 by the additional distance of the catheter 44 in the X plane. The second electrode is probably also partially shielded from the pertinent near field source by the insulated catheter filament 57', which rests between the electrode 56', 58' and the atrial wall 24.

Another significant difference from the ring electrode configuration of FIGS. 3A and 3B is that the dimension $D_4$ can be minimized as in the embodiment of FIGS. 5A and 5B so as to limit the averaging of unequal isopotential lines in the plane normal to the atrial wall 24, at least in the angular position shown in FIG. 6A.

When the filament 44 is rotated 90°, as in FIGS. 6C and 6D, the advantage of this embodiment compared to the ring electrodes of FIGS. 3A and 3B is not so apparent. Signal summation, as described previously, can occur in this orientation, since both electrodes are equidistant from atrial wall 24. Signal addition would require that the dimension $D_3$ be tuned to the extracellular wavelength of 2 to 3 mm. The need for optimization of the electrode surface area and shape factor is essentially the same as in the embodiment of FIGS. 5A and 5B as is the need for spacing the electrodes 56', 58' apart by a distance greater than 3 mm to account for anomalous behavior of the conduction system.

An even more optimal design may be the embodiment of the catheter electrodes 56", 58" shown in FIGS. 7A and 7B. The practical constraints of a catheter design, coupled with the need to interconnect the catheter to an implanted pacemaker (not shown) in a wet environment dictates design principles that require compromise from the theoretically optimum configuration of Z-axis bipolar differential detection. Because of lead diameter constraints, of practical electrode source impedance limits, and of lead angular placement uncertainties, the optimal design may be of hemicyclical electrodes 56", 58" having dimensions which circumferentially substantially encompass half of the circumference of the filament 44. In other words, dimension $D_5$ of either electrode 56" and 58" is substantially 180°, thus minimizing gradient potential averaging, yet maintaining the surface areas electrodes 56", 58" in the 4 to 6 mm$^2$ range. This surface area represents a present practical limitation imposed by pacemaker lead interwire impedances and the impedances of the pacemaker lead/pulse generator interface at the connection site resulting from the wet conductive environment.

For uses with acute instrumentation systems, however, the electrode sizes could be in 1 mm$^2$ range, provided the acute interwire impedances of the filament were high, relative to the surrounding conducting medium in which a reference electrode is placed. In the embodiment of FIGS. 7A and 7B, if the filament diameter $D_2$ is in the range of 2 mm, an electrode width $D_1$ of about 1.27 and a dimension $D_5$ in the hemicyclical dimension of about 3.14 mm linear length around the filament provides the minimum acceptable electrode surface area of 4 mm$^2$ for pacemaker applications.

Although the present invention has been described with primary emphasis on the preferred embodiments, it should be understood that various modifications can be made in the design and operation of the embodiments described without departing from the spirit and scope of the invention. For example, the first electrode 46 should be placed from about 10 cm to about 16 cm from the end electrode 50 and the spacing of electrodes 46 and 48 should be about 1 to 10 mm. The present embodiments are therefore to be considered in all respects as illustrative and not restrictive, the scope of the invention being indicated by the following claims rather than by the foregoing description, and all changes which come within the meaning and range of equivalency of the claims are therefore to be embraced therein.

What is claimed is:

1. A method for enhancing the detection of atrial P-waves using a catheter lead and a cardiac pacemaker in which stimulating pulses are generated for delivery to the heart according to physiological need of the patient determined by signals obtained solely from the detection of naturally occurring P-waves propagating through the artrial myocardial tissue, said method comprising implanting a single catheter lead having a stimulating electrode at the distal end thereof and a pair of sensing electrodes thereon longitudinally spaced apart on opposite sides of the catheter from each other and from said distal end of the lead, by introducing the lead into the right atrial and ventricular chambers of the heart via the patient's vascular system such that both of said sensing electrodes reside unrestrained within the right atrium with the lead substantially parallel to the tissue wall when the distal end of the lead is positioned at the apex of the right ventricle, measuring the approximate separation between adjacent positive and negative peaks of an average P-wave for the recipient and longitudinally spacing the sensing electrodes to approximate the separation between adjacent positive and negative peaks of the naturally occurring average atrial P-wave for the patient in which the lead is implanted, connecting the lead at its proximal end to the pacemaker so that conductors in the lead separately electrically connected to said stimulating electrode and said pair of sensing electrodes are thereby electrically connected to the pulse generator and sense circuitry, respectively, of the pacemaker, and additively combining in the sense circuitry of the pacemaker the respective signals on the separate conductors of the lead connected to each of said sensing electrodes resulting from detection of a P-wave, to enhance said P-wave detection.

2. A catheter for use in a cardiac pacemaker system, said catheter having only an electrode pair arrangement limited to two electrodes operating together in a bipolar configuration for sensing cardiac depolarization signals without requiring contact with cardiac tissue, said electrode pair axially configured on the catheter relative to the cardiac depolarization wavefront direction, to prevent signal cancellation and excess signal mitigation when the signals sensed from each electrode of the pair are electronically processed by the pacemaker system, said electrode pair is further configured such that the electrodes are placed on opposite sides relative to the catheter's, longitudinal axis and displaced longitudinal along the axis of the catheter and substantially parallel to the axis of depolarization to provide for control of the electrode dimensions in three planes to minimize field averaging in said planes and prevent signal cancellation as the depolarization wave passes each electrode.

3. A method for sensing cardiac depolarization in a cardiac pacemaker system comprising the steps, arranging an electrode pair of only two electrodes axially on a catheter, operating said electrode pair in a bipolar configuration, determining the cardiac depolarization signal length while the electrode pair is not in contact with cardiac tissue, configuring the electrode pair on the catheter relative to the cardiac depolarization signal wavefront direction to prevent signal cancellation or signal mitigation when the signals sensed from each of the pair of electrodes are electronically processed by the pacemaker system, configuring the electrode pair on opposite sides of the catheter and displaced longitudinally a distance equal to the length of the depolarization signal along the axis of the catheter substantially parallel to the axis of depolarization, such that the combinational features of controlling the electrode dimensions in each of three planes to minimize field averaging in all planes prevents signal cancellation as the depolarization wave passes each electrode.

4. The method, as defined in claim 3, further including the step of placing the electrode pair in a blood pool.

* * * * *